United States Patent [19]
Ishihara

[11] Patent Number: 4,753,527
[45] Date of Patent: Jun. 28, 1988

[54] VISUAL ACUITY TESTING APPARATUS

[75] Inventor: Taketoshi Ishihara, Tokyo, Japan

[73] Assignee: Kigaku Kikai Kabushiki Kaisha, Tokyo, Japan

[21] Appl. No.: 945,944

[22] Filed: Dec. 24, 1986

[30] Foreign Application Priority Data

Dec. 28, 1985 [JP] Japan ............................ 60-299191
Dec. 28, 1985 [JP] Japan ............................ 60-299192

[51] Int. Cl.$^4$ .................................................. A61B 3/02
[52] U.S. Cl. ..................................... 351/244; 351/239; 351/245
[58] Field of Search ............. 351/200, 237, 245, 222, 351/223, 243, 244, 239

[56] References Cited
U.S. PATENT DOCUMENTS 4,298,253 11/1981 Tagnon ............................ 351/222

Primary Examiner—Rodney B. Bovernick
Assistant Examiner—P. M. Dzierzynski
Attorney, Agent, or Firm—Finnegan, Henderson, Farabow, Garrett and Dunner

[57] ABSTRACT

A visual acuity testing apparatus is herein disclosed which comprises a test chart displayer having a display surface pointing to an upward direction; a first reflector, for downwardly reflecting a light beam from the test chart displayer, disposed above the displayer; and a second reflector for reflecting the light beam, reflected by the first reflector, towards eyes to be tested.

Said test chart displayer and the first reflector for reflecting and propagating the light beam from the displayer are contained in a leg of a table and the second reflector for reflecting the light beam from the first reflector towards the eyes to be tested is supported by a supporting arm of the table.

10 Claims, 4 Drawing Sheets

F I G. 1
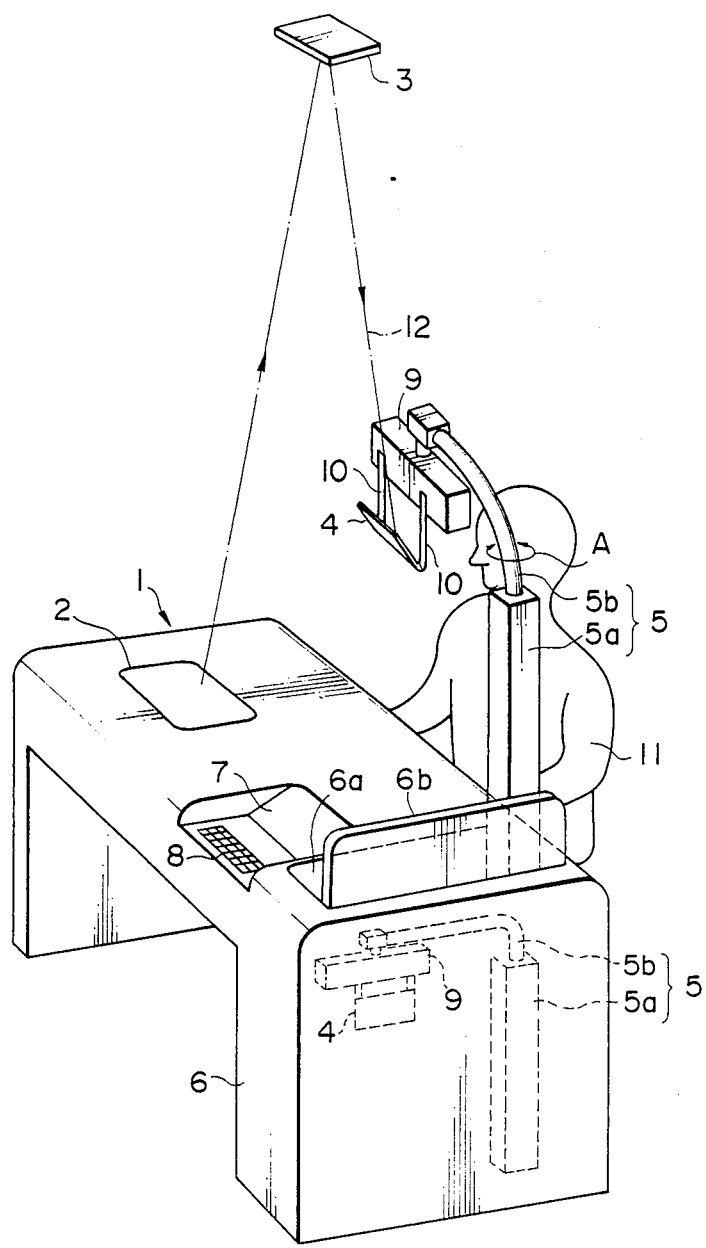

F I G. 3
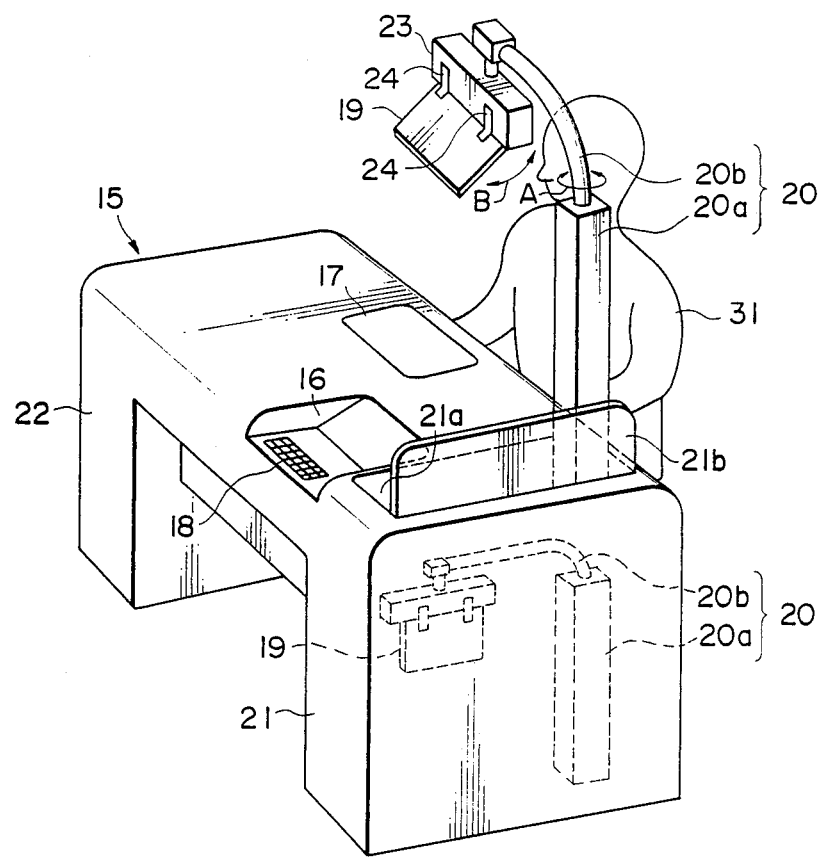

VISUAL ACUITY TESTING APPARATUS

BACKGROUND OF THE INVENTION

1. Field of the Invention

The present invention relates to a visual acuity testing apparatus, more particularly, the present invention pertains to a visual acuity testing apparatus of a subjective type used for inspecting visual acuity.

2. Related Art Statement

In conventional subjective type visual acuity testing apparatuses, it is required to lengthen the distance between an eye to be tested and an apparatus for inspecting visual acuity in order to eliminate an influence due to the ability of accommodation of the eye and therefore, these apparatuses have been constructed so that a visual acuity table is placed at 6 meters distant from the eye to carry out the inspection of visual acuity.

For that reason, a quite wide space for carrying out the visual acuity inspection should be secured when using such a conventional subjective visual acuity testing apparatus. However, it is particularly difficult for opticians and ophthalmologists to secure or maintain such wide space since, in general, the floor area thereof is very small and limited.

Moreover, in the conventional subjective visual acuity testing apparatuses, a support arm is vertically disposed on and fixed to the top of a table to support a unit for inspecting visual acuity at an upper portion of the support arm.

When such a subjective visual acuity testing apparatus is used to inspect eyes, it is also necessary to secure a space to be occupied by a consultant other than the space for eye examination.

However, it is quite difficult for opticians and ophthalmologists, the floor areas of which are quite small, to secure both areas for carrying out eye examination and consultation.

SUMMARY OF THE INVENTION

As seen from the above description, conventional subjective visual acuity testing aparatuses have a variety of disadvantages to be eliminated. Accordingly, there has been a strong need for visual acuity testing apparatus which have not such disadvantages or drawbacks.

Thus, the principal object of this invention is to provide a visual acuity testing apparatus having a simple structure and permitting the eye examination within a quite narrow space (floor area) compared with conventional apparatuses.

Another object of this invention is to provide a visual acuity testing apparatus having a single construction and making it possible to carry out eye examination and consultation within the same space.

A further object of this invention is to provide a supporting apparatus for a visual acuity testing apparatus.

The above mentioned and other objects of this invention can be achieved by providing a new visual acuity testing apparatus which comprises a test chart display means having a display surface pointing to upward direction; a first reflecting means, disposed above the test chart display means, to downwardly reflect a light beam from the test chart display means; a support arm means; a second reflecting means, supported by the support arm means, for reflecting the light beam reflected by the first reflecting means towards eyes to be tested.

According to another aspect of this invention, the visual acuity testing apparatus comprises a table provided with at least one leg; a test chart display means capable of being contained in the leg; a first reflecting means, disposed in the table, for reflecting a light beam from the test chart display means; a support arm means disposed in the table; and a second reflecting means, supported by the support arm means, for reflecting the light beam reflected by the first reflecting means towards eyes to be tested.

These and other object, features and advantages of the present invention will be well appreciated upon reading of the following description of the invention when taken in conjunction with the attached drawing with understanding that some modifications, variations and changes of the same could be made by the skilled person in the art to which the invention pertains without departing from the spirit of the invention or the scope of claims appended hereto.

BRIEF DESCRIPTION OF THE DRAWINGS

The visual acuity testing apparatus according to the present invention will hereunder be explained in more detail with reference to the accompanying drawings; wherein FIG. 1 to 4 show diagrams illustrating the visual acuity testing apparatuses according to the present invention, more specifically, FIG. 1 is an illustrative structural diagram showing an embodiment of the visual acuity testing apparatus in which the first reflector is arranged on the ceiling of the chamber or room for carrying out the eye examination;

FIG. 2 is an illustrative structural diagram showing another embodiment of the visual acuity testing apparatus in which the first reflector is disposed on the ceiling of the eye examination room, while the second reflector is mounted to the subjective testing means for inspecting visual acuity;

FIG. 3 is an illustrative structural diagram showing a further embodiment of the visual acuity testing apparatus in which the first reflector is disposed in the table; and FIG. 4 is a diagram illustrating the arrangement of the reflectors of the visual acuity testing apparatus shown in FIG. 3 and its optical path.

DETAILED DESCRIPTION OF THE EMBODIMENTS

Figure 2:
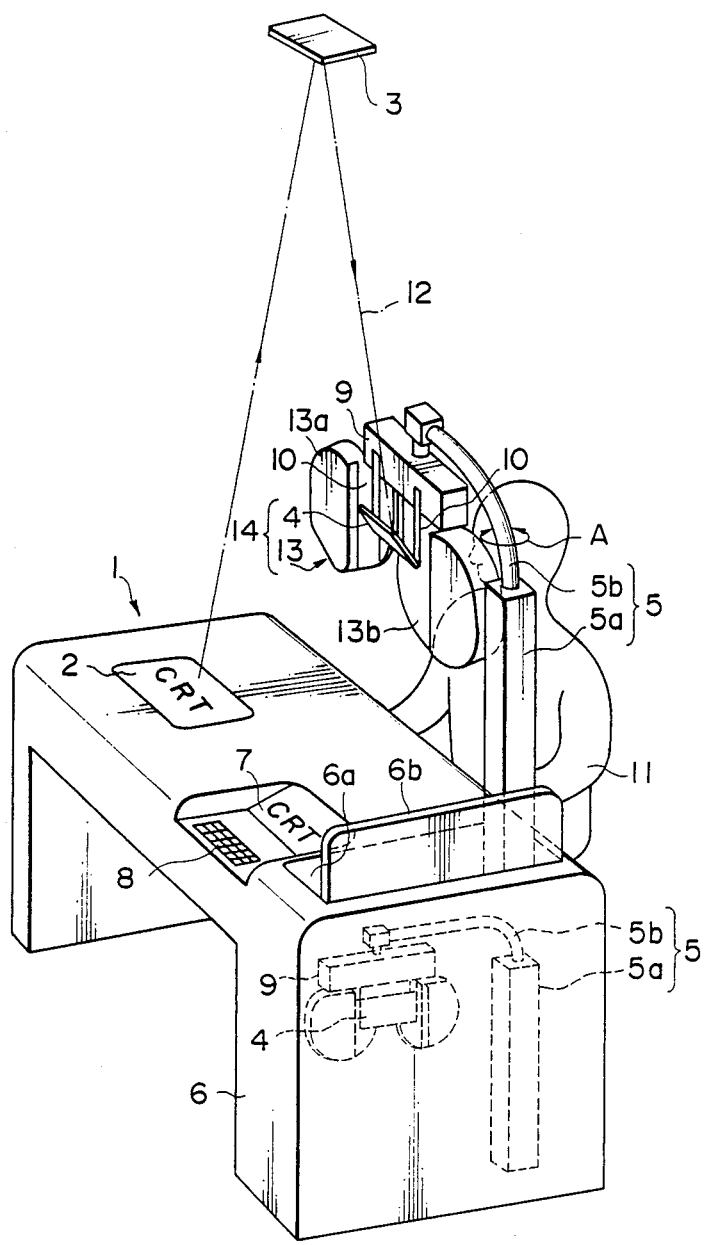

In the following, the present invention will be described in more detail with reference to preferred embodiments shown in the drawings.

<First Embodiment>

Now referring to FIG. 1, the first embodiment of the visual acuity testing apparatus according to this invention is shown. In FIG. 1, a table 1 is placed in a room (not shown) for the eye examination and on the table 1, there is disposed a test chart display means (CRT) 2 i.e., a visual acuity table display means for exhibiting a test chart to a subject to be examined. The display surface of the CRT 2 is placed on the table 1 in the manner that the level of the display surface is equal to that of the table surface and points in an upper direction towards the ceiling (not shown) of the eye examination room. The first reflecting mirror 3 may be disposed on the ceiling (not shown) of the eye examination room as the first reflecting means or the first reflector. However, the present invention is not limited to placing mirror 3 on the ceiling of the eye examination room. Alternatively, a freely expansible support prop having a flat portion at the upper extremity thereof can be mountied on the table 1 and the mirror 3 can be disposed on the flat portion. Moreover, the support porp may be designed to be a separate member independent of the table and may be arranged by one side of the table.

In FIG. 1, the reference numeral 4 represents a second reflector serving as the second reflecting mirror on the second reflecting means, the reference numeral 5 a support arm for the mirror, freely expansible (i.e., a support means), 6 a leg disposed to one of the sides of the table 1, 6a a chamber for containing a mirror formed within the whole leg and 6b a lid for opening or closing an opening located at the top of the chamber 6a for containing mirrors.

The support arm 5 for supporting mirrors is formed in an approximately L-shaped form and comprises a prop 5a constructed by, for instance, a telescopic pipe so as to freely be expanded and a bent arm 5b mounted on the top extremity of the prop 5a and capable of free rotation in a horizontal plane in the direction of an arrow A. Such a prop 5a of the support arm 5 for supporting a mirror is uprightly mounted and fixed to the bottom of the chamber 6a at its front part. A support member 9 for supporting a mirror is secured to the extremity of the bent arm 5b and a second reflecting mirror 4 is mounted to a lower part of the support member 9 through stays 10, 10. According to the construction of the visual acuity testing apparatus, the second reflecting mirror 4 can be contained within the chamber 6 for containing the same due to the telescopic movement of the support arm 5 when the eye examination is not effected.

In addition, on the table 1 there is provided a CRT 7 for the operator (or inspector), on which data obtained during the eye examination or the like are displayed.

Furthermore, in the second reflecting mirror 4, the CRT 2 for the subject to be tested is projected through the first reflecting mirror 3. This second reflecting mirror 4 is not vertically disposed on the support member 9 as shown in FIG. 1 and is inclined at a desired angle so that the CRT 2 is reflected to the eyes of the subject to be examined through the first mirror 3. CRT 2 and CRT 7 are designed so that a digital image of the test chart is displayed with the operation of a key board 8.

The visual acuity testing apparatus as shown in FIG. 1 may be operated as will be explained below:

According to the apparatus having the structure explained above, images of the CRT 2 as the visual acuity table displayer reach the eyes of the subject 11 to be examined in the manner such that the images of the CRT 2 are first projected to the first mirror 3, then reflected by the mirror 3 towards the second reflecting mirror 4 along the optical path 12 and thereafter reflected towards the eyes of the subject 11. In this manner, the subject 11 is subjected to the eyes examination.

This embodiment makes it possible to easily carry out the eye examination and project a variety of images of the test chart since the test chart is just before the subject due to the use of the CRT 2, 7 as the visual acuity table displayer differing from those conventional wall type or projector type apparatus. Moreover, it is also possible for a subject to view a specific part of the test chart. The inspector can always recognize the data obtained during the eye examination by monitoring the CRT. This is because CRT image specific to the subject to be examined and that image specific to the inspector are separately disposed. A printer can also be included in the apparatus to print out data.

When the eye examination is not carried out, support arm 5 provided with the second reflecting mirror 4 can be contained within the table 1 i.e., the chamber 6a formed within the leg 6 of the table and therefore, the specific space required for a consultant is not limited to using a space above the table 1.

According to a variation of such embodiment, the CRT may be substituted with a combination of a projector and a screen or those composed of a liquid crystal or a visual acuity table card.

<Second Embodiment>

Referring to the attached FIG. 2, there is shown the second embodiment of the present invention. This embodiment corresponds to that of the first embodiment explained above except that a subjective testing means 13 i.e., a device for testing the refractive power of eyes to be tested as the testing means is installed to the support means 9 for supporting mirror. Moreover, in this embodiment, a testing unit 14 is comprised of the subjective testing means 13 for measuring the refractive power of eyes and the second reflecting mirror 4 (the second reflector).

This subjective testing means 13 is provided with inspecting members 13a and 13b for measuring the refractive power of right-hand eye and left-hand eye respectively. Both of inspecting members 13a, 13b are provided with a lens unit (not shown) containing a series of lenses for inspection placed at the level of the eyes of a subject. On each wall of the inspecting members 13a, 13b, there is formed a sight-through hole (not shown) through which a subject 11 to be examined can see the second reflecting mirror 4 through the series of lenses. In this connection, the structure of the testing means 13 is well known and therefore, the concrete structure thereof is not shown in the Figs.

Furthermore, the second reflecting mirror is not placed vertically as shown in FIG. 2 and the angle of the mirror can be adjusted so that the light beam from CRT 2 exactly reaches the eyes of a subject through the reflecting mirrors 3 and 4.

According to the apparatus having the construction explained above, the eye examination can be carried out by, for instance, demounting the lens located at either the inspecting member for right-hand eye (13a) or that for left-hand eye (13b) of the testing means 13 from the sight-through hole to make one of the sight-through holes vacant, in the manner similar to that of the first embodiment. Moreover, the refractive power of the subject 11 can be inspected if the lens for inspecting the same are mounted to the sight-through hole.

In addition, the testing unit 14 is supported by the support arm 5 which is freely expansible and horizontally rotatable and therefore, the unit 14 can be moved so as to face toward the eyes of the subject to be examined during the eye examination, while the unit 14 can be contained within the chamber 6a as is shown by the broken line in FIG. 2 when the unit does not serve to examine the subject.

<Third Embodiment>

Referring now to the attached FIG. 3, there is shown the third embodiment of the present invention.

In FIG. 3, a CRT 16 for inspector and a glass window 17 are disposed on the top surface of a table board i.e., on the top surface of the table 15 and a key board 18 for operating the test chart is arranged at the vicinity of the CRT 16 for inspector.

Other members are, in FIG. 3, a fifth reflecting mirror 19 as the second reflecting means i.e., the second reflector which is placed over the glass window 17, a mirror-supporting arm 20 as the support means disposed at one side of the table 15, a first leg 21 mounted to the table 15 at one side thereof, a mirror-containing chamber 21a formed within the leg. 21, a lid 21b for opening or closing an opening at the top of the mirror-containing chamber 21a and a second leg 22 mounted to the table 15 at the other side thereof.

The mirror-supporting arm 20 is in an L-shaped form and comprises a prop 20a constructed by, for instance, a telescopic pipe so that the arm is freely expansible; and a bent arm 20b installed to the upper extermity of the prop 20a and freely rotatable in a horizontal plane in the direction shown by an arrow A. Such a prop 20a of the mirror-supporting arm 20 is uprightly mounted and fixed to the bottom of the mirror-containing chamber 21a. A mirror-supporting member 23 is fixed to the extremity of the bent arm 20b and fifth reflecting mirror 19 is mounted at the lower portion of the mirror-supporting member 23 so as to be adjustably rotatable in the direction of an arrow B, through an angle-adjusting device 24, 24. According to such construction, the fifth mirror 19 can be contained in the mirror-containing chamber 21a i.e., within the first leg 21 of the table 15 due to the telescopic movement of the mirror-supporting arm 20 if the eye examination operation is not carried out.

Figure 4:
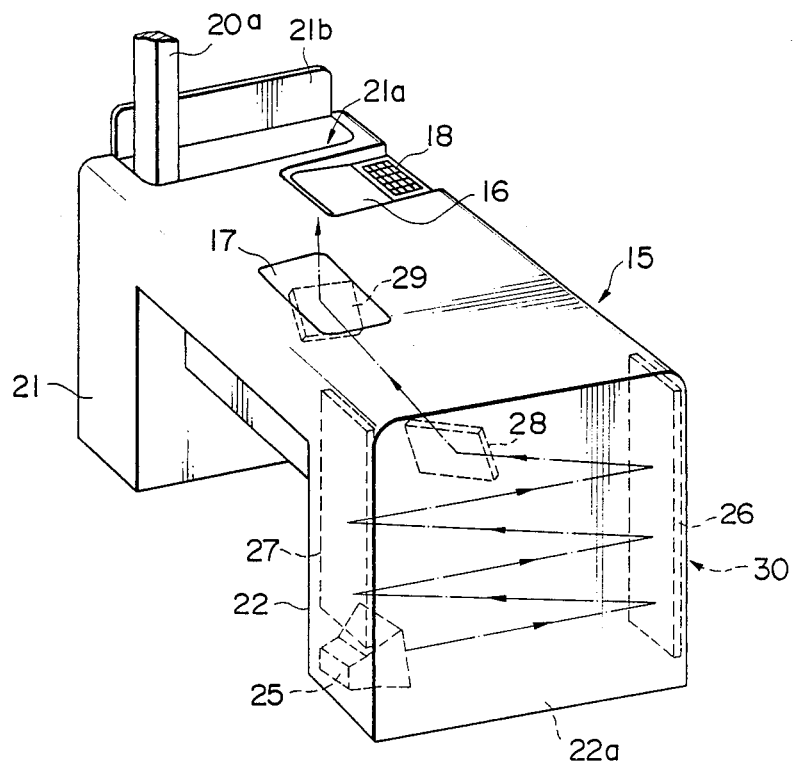

As seen from FIG. 4, a mirror-containing chamber 22a is formed within the whole of a second leg 22 of the table 15, on the bottom of which a CRT 25 for subjects to be examined is disposed near the front wall thereof and a first reflecting mirror 26 is uprightly mounted and bonded to the back wall of the chamber 22a, faced toward the front wall.

A second reflecting mirror 27 is uprightly mounted and bonded to the front wall so as to face to the first mirror 26 and a third reflecting mirror 28 is maintained at the upper and central portion of the mirror-containing chamber 22a. The third mirror 28 serves to reflect a light beam, which is directed to the mirror 28 after a multiple reflection between the first and second reflecting mirrors 26, 27, in a direction almost parallel to the surface of the table 15. Moreover, a fourth reflecting mirror 29 is disposed under the glass window 17 placed on the top surface of the table 15 and serves to reflect the light beam reflected by the third reflecting mirror 28, towards the fifth reflecting mirror 19 as the second reflecting means. On the display surface of CRT 16, the same test chart as in the CRT 25 is displayed.

The light beam coming out of the CRT 25 is reflected several times between the reflecting mirrors 26 and 27, then reflected in turn by the third reflecting mirror 28, the fourth mirror 29 and the fifth mirror 19 and directed towards the front part of the table 15. These reflecting mirrors 26,27,28 and 29 constitute the first reflector 30.

The apparatus for inspecting functions of eyes having the structure explained above will be operated in the manner described below.

On the display surface of both CRT 25 and CRT 16 for the subject to be examined and for the inspector respectively, an identical test chart composed of digital signals is displayed by the operation of the key board 18. A light beam coming out of the CRT 25 for the subject to be examined is subjected to a multiple reflection between the reflecting mirrors 26 and 27 and then deflected towards the fourth mirror 29 due to the presence of the third reflecting mirror 28. The deflected light beam passes through the glass window 17, is again deflected towards eyes with the fifth mirror 19 and reaches the eyes of the subject to be examined situated at the eye examination part.

In this embodiment, the mirror-supporting arm 20 provided with the fifth mirror 19 can be contained in the table 15 i.e., within the mirror-containing chamber 21a as is shown by the broken line in FIG. 3 and thus, the eye examination and the consultation can be carried out within the same space, that is, there is no need for special consulting space.

Due to the fact that CRT is used as the test chart displayer and that, as a result, the test chart is present just before the subject and the inspector, it becomes possible to facilitate the observation of the test chart and display a variety of images on the display surface compared with the conventional apparatus such as a wall type or projector type. Moreover, the inspector can confirm the test chart situated just before him since CRTs' specific to subjects to be examined and inspectors are separately disposed in the apparatus.

In this embodiment, the apparatus may be designed so that each key of the key board is provided with a lamp capable of independently switching on or off and each lamp of the key interested on the key board is turned on during displaying, instead of using the CRT 16 for inspector.

As other examples, the CRT as the test chart displayer may be replaced with those constructed by a combination of a projector and a screen, or a liquid crystal or visual acuity table card. If the second reflector of this embodiment is installed to the apparatus for determining the reflective power of eyes as explained in the description of the second embodiment, the inspection of the refractive power is also possible.

The visual acuity testing apparatus according to the present invention has hereinbefore been explained in detail with reference to the illustrative and preferred embodiments. However, it is not intended to restrict the scope of this invention to those specific embodiments as set forth above, on the contrary, it should be appreciated that the present invention includes various kinds of variations, alternatives, modifications and equivalents as may be included within the scope and spirit of this invention as defined by the appended claims.

What is claimed is:

1. A visual acuity testing apparatus comprising:
   (a) a table having a test chart display means disposed therein, said test chart display means having a display surface which points toward an upward direction relative to said table;
   (b) a first reflecting means, disposed above said test chart display means, to downwardly reflect a light beam from the test chart display means;
   (c) a support arm means;
   (d) a second reflecting means, supported by said support arm means, for reflecting the light reflected by said first reflecting means towards eyes to be tested.

2. The visual acuity testing apparatus as set forth in claim 1 wherein a subjective testing means for determining refractive power of the eyes to be tested is supported by the support arm means and the second reflecting means is incorporated in the subjective testing means.

3. The visual acuity testing apparatus as set forth in claim 1 wherein the table is provided with at least one leg and the support arm means is removably contained in said leg.

4. The visual acuity testing means as set forth in claim 2 wherein said table is provided with at least one leg and said support arm means is removably contained in said leg.

5. A visual acuity testing apparatus comprising:
   (a) a table having at least one leg;
   (b) a test chart display means capable of being contained in the leg;
   (c) a first reflecting means for reflecting a light beam from the test chart display means, disposed in the table;
   (d) a support arm means disposed on the table;
   (e) a second reflecting means for reflecting the light beam reflected by the first reflecting means towards eyes to be tested, which is supported by the support arm means.

6. The visual acuity testing apparatus as set forth in claim 5 wherein a subjective testing means for determining refractive power of the eyes to be tested is supported by the support arm means and the second reflecting means is mounted to the subjective testing means.

7. The visual acuity testing apparatus as set forth in claim 5 wherein the table is provided with two legs, one of which contains the test chart display means and a part of the first reflecting means and the other of which removably contains the support arm means.

8. The visual acuity testing apparatus as set forth in claim 6 wherein the table is provided with two legs, one of which contains the test chart display means and a part of the first reflecting means and the other of which removably contains the support arm means.

9. The visual acuity testing apparatus as set forth in claim 5 wherein the first reflecting means comprises first and second mirrors which are vertically disposed in the leg of the table so that said first mirror faces said second mirror; a third mirror, for reflecting said light beam from the first and second mirrors after a multiple reflection of said light beam therebetween in an approximately parallel direction with respect to a surface of a table board of the table; and a fourth mirror for reflecting the light, reflected by the third mirror, towards the second reflecting means.

10. A supporting apparatus for a visual acuity testing means comprising:
   (a) a table provided with at least one leg;
   (b) a supporting means comprised of a freely expansible prop and an arm for supporting a visual acuity testing means to determine refractive power of eyes to be tested, said testing means being mounted to an upper end of the prop so as to be able to rotate in a horizontal plane;
   (c) a chamber for containing the supporting means and the visual acuity testing means supported by the supporting means, said chamber being formed within the leg of the table, whereby, during a visual acuity test, said visual acuity testing means is operably arranged so as to face to a position at which eyes to be tested are located by expanding the prop and rotating the arm while, when the visual acuity test is not being carried out, said visual acuity testing means and said supporting means are movable into said chamber.

* * * * *

UNITED STATES PATENT AND TRADEMARK OFFICE
CERTIFICATE OF CORRECTION

PATENT NO. : 4,753,527

DATED : June 28, 1988

INVENTOR(S) : Ishihara

It is certified that error appears in the above-identified patent and that said Letters Patent is hereby corrected as shown below:

Title page:

Assignee: "Kigaku Kikai Kabushiki Kaisha" should be --Tokyo Kogaku Kikai Kabushiki Kaisha--.

Signed and Sealed this

Twenty-first Day of February, 1989

Attest:

DONALD J. QUIGG

*Attesting Officer*  *Commissioner of Patents and Trademarks*